US005629183A

United States Patent [19]

Saunders et al.

[11] Patent Number: 5,629,183

[45] Date of Patent: May 13, 1997

[54] PLANT TRANSFORMATION BY GENE TRANSFER INTO POLLEN

[75] Inventors: James A. Saunders, Dayton; Benjamin F. Matthews, Laurel, both of Md.

[73] Assignee: The United States of America as represented by the Secretary of Agriculture, Washington, D.C.

[21] Appl. No.: 345,869

[22] Filed: Nov. 28, 1994

Related U.S. Application Data

[63] Continuation of Ser. No. 530,485, Jun. 1, 1990, abandoned, which is a continuation of Ser. No. 350,356, May 8, 1989, abandoned.

[51] Int. Cl.$^6$ ..................................................... C12N 15/09
[52] U.S. Cl. ..................... 435/172.3; 435/172.1; 800/205; 800/DIG. 43; 800/DIG. 56
[58] Field of Search .............................. 435/172.1, 172.3; 800/205, DIG. 43, DIG. 56

[56] References Cited

U.S. PATENT DOCUMENTS

| | | | |
|---|---|---|---|
| 4,940,835 | 7/1990 | Shan et al. | 800/205 |
| 5,049,500 | 9/1991 | Arnizen et al. | 435/172.3 |
| 5,066,594 | 11/1991 | DeBonte et al. | 435/240.4 |
| 5,384,253 | 1/1995 | Kryzek et al. | 435/172.3 |

FOREIGN PATENT DOCUMENTS

| | | | |
|---|---|---|---|
| 1327173 | 2/1994 | Canada . | |
| 0270356B1 | 1/1994 | European Pat. Off. | C12N 15/82 |
| 8501856 | 5/1985 | WIPO | 435/172.1 |
| WO8900602 | 1/1989 | WIPO . | |

OTHER PUBLICATIONS

Neumann, E., and Bierth, P., Gene Transfer by Electroporation, *American Biotechnology Laboratory*, publ. Monthly by International Scientific Communications, Fairfield, CN, vol. 4, No. 2, Mar./Apr. 1986, pp. 10–15.

Riggs, Charles Daniel, and Bates, George W., "Stable transformation of tobacco by electroporation: Evidence for plasmid concatenation", *Proc. Natl. Acad. Sci. USA*, vol. 83, Aug. 1986, Genetics, pp. 5602–5606.

Christou, Paul, et al., "Stable transformation of soybean by electroporation and root formation from transformed callus", *Proc. Natl. Acad. Sci. USA*, vol. 84, Jun. 1987, Applied Biology, pp. 3962–3966.

K. P. Mishra et al., "In vitro Electroporation of Tobacco Pollen," Plant Sci. 52: 135–139 (1987).

Stephen Berberich, "USDA Plant Molecular Biology Laboratory to Open," Research News (Mar. 25).

Mishra et al (1987) Plant Science 52: 135–139.

Ohta (1986) Proc. Natl. Acad. Sci., USA 83: 715–719.

Sanford (1988) in *Forest and Crop Biotechnology: Progress and Prospects*; Colloquium pp: 163–173 Springer Verlag, NY, 1988.

Negrutiu, et al "Pollen: International Conference.", Amherst, MA, USA, Jun. 1985, pp. 65–70.

Pan, et al (Mar. 31, 1989) Maize Genetics Cooperation Newsletter #63:20.

Potrykus (Jun. 1990) Bio/Technology 8:535–542.

Mathews et al (1990) Sex Plant Reprod. 3(3):147–151.

Abdul-Baki, et al (1990) Plant Science 70(2):181–190.

Negrutiu, I, et al., "Attempts to Transform for Kanamycin-Resistance in Mature Pollen of Tobacco," *Biotechnology and Ecology of Pollen*, Proceedings of the International Conference on the Biotechnology and Ecology of Pollen, 9–11 Jul. 1985, Univ. of Massachusetts, Amherst, MA, pp. 65–70.

*Primary Examiner*—Che S. Chereskin
*Attorney, Agent, or Firm*—M. Howard Silverstein; Curtis P. Ribando; John D. Fado

[57] ABSTRACT

Plant germplasm is transformed with foreign DNA by introducing the DNA into pollen grains by a technique such as electroporation, mating ova of the desired plant line with the transformed pollen, and selecting for the transformed germplasm. The germinating pollen, resultant seed, and the progeny can each be screened for expression of the foreign gene. The transformed pollen can be used as a vector for introducing the foreign DNA into plant lines of similar or dissimilar origin, including both monocots and dicots.

12 Claims, 4 Drawing Sheets

PLANT TRANSFORMATION BY GENE TRANSFER INTO POLLEN

This application is a continuation of application Ser. No. 07/530,485, filed Jun. 1, 1990, now abandoned, which is a continuation of 07/350,356, filed May 8, 1989, now abandoned.

BACKGROUND OF THE INVENTION

1. Field of the Invention

Present-day gene transfer techniques allow the possibility for the development of more productive crop plants at a pace much faster than before. Gene transfer and selection of the best plants has been the objective of breeding programs for years. Powerful new techniques for gene transfer recently have been developed for moving single genes and whole blocks of genes from one plant to another and even for moving genes from non-plants into plants. These new techniques can help mankind preserve the genetic diversity of plants by actually creating greater diversity through gene recombination.

This invention relates to a novel method for producing transformed germplasm which circumvents many of the limitations associated with the present-day technology in this field.

2. Description of the Prior Art

Several methods have been developed for the transformation of eucaryotic cells of plants and animals by foreign DNA. These methods include protoplast fusion [W. Schaffner, Proc. Nat'l. Acad. Sci. U.S.A. 77: 2163–2167 (1980); M. Rassoulzadegan et al., Nature 295: 257–259 (1982)], DEAE dextran [J. H. McCutchan et al., J. Nat'l. Cancer Inst. 41: 351–357 (1968)], calcium phosphate coprecipitation with DNA or recombinant bacteriophage [F. L. Graham et al., Virology 52: 456–467 (1973); M. Ishiura et al., Mol. Cell. Biol. 2: 607–616 (1982)]. More recently, electroporation has been successful in introducing DNA into plant protoplasts [M. Fromm et al., Proc. Nat'l. Acad. Sci. U.S.A. 82: 5824–5828 (1985); M. Fromm et al., Nature 319: 791–793 (1986)], fibroblasts [H. Liang et al., Biotechniques 6: 550–558 (1988)], and mammalian rod blood cells [T. Y. Tsong et al., Biblio. Haematol. 51: 108–114 (1985); G. Chu et al., Nucl. Acids Res. 15: 1311–1326 (1987)]. The success of the electroporation method is dependent, in part, on optimizing parameters relative to the membrane, the DNA, and the electric field. Evidence for the success of transformation after electroporation has been measured by incorporation of radioactively labeled DNA [Tsong et al., supra], transient gene expression [H. Potter et al., Proc. Nat'l. Acad. Sci. U.S.A. 81: 7161–7165 (1984); O. Smithies et al., Nature 317: 230–234 (1985)], and the formation of stable transformants [C. D. Riggs et al., Proc. Nat'l. Acad. Sci. U.S.A. 83: 5602–5606 (1986); H. Stopper et al., Z. Naturforsch. 40c: 929–932 (1985)].

There are several drawbacks to current methods of DNA transformation in plants. One of these is that the transfer of DNA usually involves the use of isolated protoplasts. Protoplasts from many plant species are recalcitrant to regeneration into mature genetically stable plants and many of the most important economic crop plants have never been regenerated from protoplasts. In most cases where regeneration has been achieved, the production of plants from transformed protoplasts involves lengthy sterile culture and regeneration procedures. Further, many DNA transformation procedures involve the use of *Agrobacterium tumefaciens*, and its tumor-inducing (Ti) plasmid. The number of plant species that are infected by this system is extremely limited, and other vectors are not currently available.

SUMMARY OF THE INVENTION

We have now surprisingly discovered that foreign DNA can be introduced into mature pollen grains and integrated into the pollen DNA as evidenced by expression of the foreign DNA in the germinating pollen grain. Transformed pollen can be used to fertilize ova in flowering plants and thereby obtain transformed seed and progeny plants. The germinating pollen, resultant seed, the plant propagated from the seed, and progeny thereof are readily screened to identify transformants.

In accordance with this discovery, it is an object of the invention to produce genetically engineered seed and achieve DNA transformation in all species of plants without the complications of regeneration from protoplasts or tissue culture. Another object of the invention is to effect DNA transformation in plant systems via introduction of foreign DNA (e.g., genetically engineered DNA) into pollen.

It is also an object of the invention to achieve expression of foreign DNA in transformed pollen, in seed produced by fertilizing plant ova with the transformed pollen, and in plants generated from the transformed seed.

Another object of the invention is to apply the technique of electroporation to the introduction of the foreign DNA to the pollen grains.

A further object of the invention is to apply the concept of introducing DNA into pollen to both monocotyledonous and dicotyledonous plants.

A further object of this invention is to apply the technique of electroporation to the introduction of foreign DNA to cells which differentiate into pollen such as microspore mother cells.

Other objects and advantages of this invention will become readily apparent from the ensuing description.

GLOSSARY

For purposes of this invention, the following standard abbreviations and terms used herein have been defined below. Also included are a listing of biological materials and reagents mentioned in the specification.

ABBREVIATIONS

DNA=deoxyribonucleic acid
EDTA=ethylenediaminetetraacetic acid
GUS=$\beta$-glucouronidase
SDS=sodium dodecyl sulfate
SSC=0.15M sodium chloride and 0.015M sodium citrate
UidA=gene encoding $\beta$-glucuronidase.

TERMS clone/cloning: in reference to DNA, the product or process of isolating a segment of DNA, linking it to a vector, and introducing it into a host for propagation.

DNA sequence: a linear series of nucleotides connected one to the other by phosphodiester bonds between the 3' and 5' carbons of adjacent pentoses.

electroporation: a technique for reversibly permeabilizing membranes of mammalian, plant, or microbial cells by application of high-intensity electrical impulses.

expression: the transcription of a structural gene into messenger RNA (mRNA) and the subsequent translation of the mRNA into a protein coded by the gene.

expression system: a structural gene in combination with the full complement of cellular components necessary for expression of the gene.

foreign gene: a gene not normally present in a particular genome, cell, or vector.

gene: a segment of DNA which encodes an RNA, e.g., messenger RNA, ribosomal RNA, or transfer RNA.

gene of interest: a gene which encodes a desirable RNA molecule, e.g., messenger RNA, "antisense" RNA, or "ribozyme" which is desirably expressed in a prokaryotic or eucaryotic host upon transformation of the host with the gene or a vector carrying the gene, or is expressed in vitro using appropriate medium and enzyme.

genome/genomic: referring to the complete set of genetic instructions for an organism as defined by the chromosomal nucleic acid.

hybridization: the pairing together or annealing of single-stranded regions of nucleic acids to form double-stranded molecules.

oligonucleotide: a DNA sequence comprising at least eight nucleotides.

phage: a bacteriophage; a virus which infects bacteria.

plant line: a taxonomic group or variety of plants which is characterized by certain genotypic and/or phenotypic traits conserved from generation to generation through inbreeding.

plasmid: a non-chromosomal, double-stranded DNA sequence capable of autonomous replication within a host cell.

probe: a nucleic acid sequence (DNA or RNA) that can be used to detect, by hybridization or complementary base-pairing, another nucleic acid sequence which is homologous or complementary.

recombinant DNA molecule: a hybrid DNA sequence comprising at least two DNA sequences, the first sequence not normally being found together in nature with the second.

sequence: two or more DNA or RNA nucleotides in a given order.

transform: to change in a heritable manner the characteristics of a host cell by the introduction of DNA foreign to that cell.

transformant/transformation system: a host cell such as a tobacco plant cell which has been transformed by introduction of a vector containing DNA foreign to the cell.

transgenic: relating to new genetic information becoming embedded into a germline.

BIOLOGICAL MATERIALS AND REAGENTS

| Plasmid | Source |
| --- | --- |
| pBI221 | Clontech (Palto Alto, CA) |

| Restriction Enzyme | Cleavage Site |
| --- | --- |
| EcoRI | 5'..G˅AATTC..3' |
| HindIII | 5'..A˅AGCTT..3' |

DETAILED DESCRIPTION OF THE INVENTION

Figure 1:
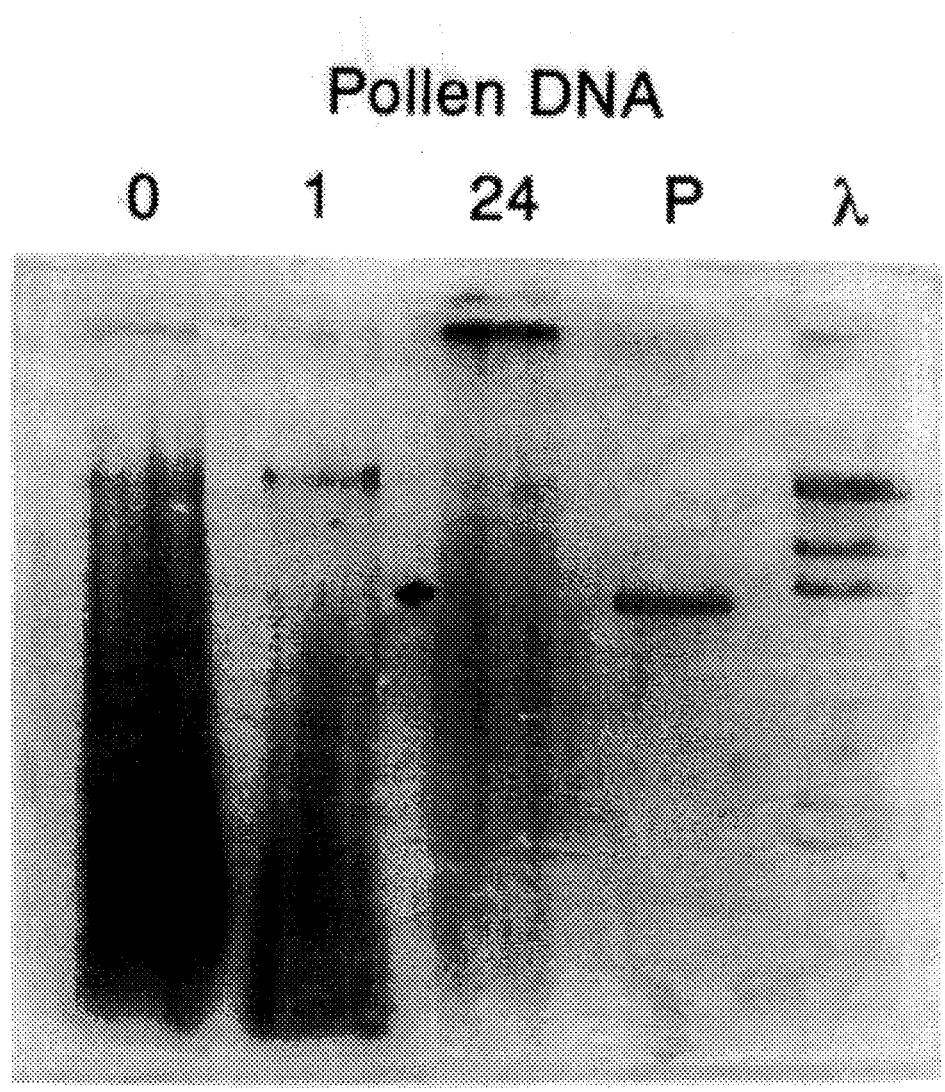
FIG. 1 is an agarose gel containing DNA extracts comparing pollen untreated and treated with GUS DNA.

The process of this invention is believed to be applicable to all species of pollen-producing plants, whether monocotyledonous or dicotyledonous. Of particular interest, of course, are agriculturally important plants, such as field crops, horticultural crops, and orchard crops. The procedures for collecting pollen from the anthers of such plants is well established, as is the procedure for artificially fertilizing the ovules (eggs) found in the plant ovaries. The collected pollen can be used immediately for DNA uptake, or it can be stored under conditions which will substantially preserve its viability. To be effective for gene transfer techniques, not only must the viability of the pollen be maintained, but the pollen tube must maintain its ability to elongate through the style of the flower to reach the ovules. For example, tobacco pollen stored within the range of −70° C. to −20° C. will retain 80–85% viability and ability for tube elongation over a period of 6 wks.

The advantages of the invention are obtained by introducing the foreign DNA into the pollen by means of electroporation. This technique results in a level of plant transformation which substantially exceeds the level of transformation achievable by other methods currently known in the art. In the preferred embodiment described herein, the electroporation is applied to germinating pollen. The relatively thin wall of the pollen tube containing the generative nucleus is readily permeabilized to be receptive to infusion of DNA. The efficacy of introducing DNA into the germinating pollen by electroporation is related to several important variables. These variables include the pulse field strength, the pulse duration, resealing time of the pores induced in the cell membrane, and the concentrations of pollen and DNA in the electroporation medium.

The field strength of the pulse is controlled by two components: the applied current and the electrode gap. To have an effective electroporation pulse, minimal threshold levels for both the pulse duration and the pulse field strength must be exceeded. It appears that the field strength of the pulse interacts with pulse duration such that, over a limited range, one variable may be increased as the other is decreased and a reversible pore may still be induced. In the case of tobacco pollen, for example, the most effective combination of pulse field strength and pulse duration for the uptake of DNA is 8 to 9 Kv/cm with a single pulse of 80 μsec. Pulses lower than 5 Kv/cm do not seem to be effective, and pulses higher than 10 Kv/cm cause loss of viability and a reduced growth of the pollen tubes.

Since pore formation by electroporation is a reversible process, the time required to reseal the induced pores becomes an important variable for the successful incorporation of foreign DNA. In germinating tobacco pollen, up to 1 hr is usually required for the membrane pores to reseal.

The level of DNA uptake is directly related to the DNA concentration up to a threshold level which perhaps reflects a saturation endpoint.

The foreign DNA to be introduced into the pollen may be in any form which will migrate into the prepared pollen and which is amenable to participation in a recombinant event with the native DNA of the pollen. For example, there are expectedly intrinsic limitations on the size of the DNA molecules which can be infused into permeabilized pollen. The DNA to be transferred to the pollen may be in the form of linear oligonucleotides, recognized gene sequences, linearized plasmids, recombinant DNA molecules, etc.

After the pollen has been treated for DNA uptake, it may optionally be assayed for expression of the DNA of interest in order to confirm the success rate of the DNA introduction. Thereafter, pollen transformation simply requires the pollen containing the foreign DNA to be placed onto a receptive stigma of an emasculated flower, and the pollen will translocate the DNA to the ovule (ovum, egg) upon fertilization. There is currently no evidence whether this translocation takes place after nuclear incorporation of the foreign DNA by the pollen nuclei or whether the foreign DNA is translocated as part of the cytoplasmic constituents of the germinating pollen grain. After seed set, the seeds are collected and germinated on selective media allowing the identification of transformants. The transformants are rescued and grown to full plants, selfed, and the resulting seed is examined for the presence of a marker gene and other incorporated genes. Transformation can also be confirmed by examining the transgenic plants which express the gene of interest as an identifiable morphological characteristic.

DNA transport by pollen may take place within the same flower and between flowers located on the same plant or on different plants. Pollination may occur within a cultivar or may involve intercultivars, interspecies, or intergenera.

The following examples are intended only to further illustrate the invention and are not intended to limit the scope of the invention which is defined by the claims.

EXAMPLE 1

Pollen Collection. Pollen was collected from tobacco plants, *Nicotiana gossie* L. Domain, grown in the greenhouse with fluorescent light to supplement and extend the natural light period. Pollen was collected in the morning and was assayed as having a moisture content of approximately 13% (w/w) and up to 90% germination. It was used immediately or preserved in a desiccator at 4° C. for up to 2 wks without loss of viability.

Pollen Germination. Due to the fragility of the germinating pollen and its tendency to stick to surfaces of glass- and plasticware, mechanical manipulations during germination and electroporation were kept to a minimum. After electroporation the pollen grains were allowed to remain in the same vessel while the pores resealed. The standard conditions for germinating the pollen before electroporation were as follows: Four milligrams of pollen were placed in a 1-ml plastic cuvette and germination was initiated by the addition of 280 μl of the pollen germination medium supplemented with 1 μg salmon sperm DNA (Sigma Chemical Co.). The germination medium consisted of 0.29M sucrose, 1.27 mM Ca $(NO_3)_2$, 0.16 mM $H_3BO_3$ and 1 mM $KNO_3$, pH 5.2, adjusted with additional $H_3BO_3$ [D. B. Dickinson, Plant Phys. 43 (1): 1–8 (1968)]. The pollen was suspended in this medium and placed on a shaker at 160 oscillations/min at 35° C. for 1 hr.

Electroporation. The electroporation chamber (BTX, San Diego, Calif.) contained 4 mg pollen germinated 1 hr in 300 μl germination medium and 20 μg linearized pBI221 DNA. The plasmid pBI 221 containing the gene encoding GUS was obtained from Clontech (Palo Alto, Calif.) and was linearized by digestion with EcoRI according to manufacturer's instructions (Bethesda Research Laboratories, Rockville, Md.). The chamber was capped with two stainless steel flat electrodes with parallel surfaces (BTX, San Diego, Calif., Model P/N 472). The germinating pollen/DNA suspension was subjected to a 9 Kv/cm 80 μsec square wave pulse. The pollen remained undisturbed for 40 min following the pulse. The electroporated pollen was transferred to sterile incubation plates in 1.1 ml of germination medium and was incubated at 35° C. for 1 or 24 hrs with continuous gentle shaking. The germinating pollen was collected by centrifugation at 100×g for 1 min.

Assay for Expression of GUS enzyme activity. For measuring GUS activity, the centrifugation pellet was resuspended in 700 μl of GUS lysis buffer [GUS Users Mannual, Clontech laboratories, Inc., Palo Alto, Calif.] containing 50 mM $NAPO_4$, pH 7.0, 10 mM EDTA, 0.1% (v/v) "Triton X-100", 0.1sarkosyl, and 10 mM β-mercaptoethanol, thoroughly ground in a chilled mortar and centrifuged at 2500×g for 10 min. Both the supernatant and pellet were assayed for GUS activity in GUS lysis buffer at 37° C. The reaction mixture consisted of 500 μl of 1 mM 4-methyl umbelliferyl β-D-glucuronide in lysis buffer and 200 μl of the pollen extract. The reaction was stopped by the addition of 0.2M $Na_2CO_3$ to bring the final volume to 2.0 ml. The activity was measured fluorometrically using wavelengths of 365 and 455 nm for excitation and emission, respectively. Quantitation of activity was established from a standard curve using umbelliferone as a standard.

GUS activity was compared between germinating pollen and germinating pollen electroporated in the presence of 5 μg linearized pBI221 containing the *E. coli* GUS gene 24 hrs after electroporation of the linearized plasmid into the pollen. The 24-hr interval was considered sufficient to allow for expression of the GUS enzyme (Table I). Only trace GUS activity was detected in the germinating pollen that was not treated with pBI221 and plasmid-treated pollen that was not electroporated. On the other hand, pollen electroporated in the presence of the plasmid and incubated for 24 hrs at 35° C., then extracted, demonstrated high GUS activity with most of the activity being recovered in the particulate fraction. The expression of GUS activity 24 hrs after applying plasmid pBI221 and electroporating provides conclusive evidence that the tobacco pollen is able to take up and express foreign DNA. GUS activity in the electroporated treatments was over 100-fold higher than that in the non-electroporated identical treatments.

TABLE I

| GUS Activity in Soluble and Particular Extracts of Electroporated Pollen | | | |
|---|---|---|---|
| Electroporation pulse | GUS DNA | Extract | Total activity umbelliferone ng/mg pollen/hr |
| + | − | soluble | 0.1 |
| − | − | particulate | 1.9 |
| − | + | soluble | 0.6 |
| − | + | particulate | 1.5 |
| + | − | soluble | 0 |
| + | − | particulate | 0 |
| + | + | soluble | 13 |
| + | + | particulate | 120 |

Extraction of DNA from Pollen. Further evidence for the uptake of plasmid DNA by pollen was provided by extracting DNA from pollen 1 hr and 24 hrs after electroporation of the pollen in the presence of pBI221. The pollen was treated with DNase to remove nonincorporated DNA from the surface. The pollen DNA was then extracted by grinding the pollen in a chilled mortar and pestle in 50 mM Tris, 10 mM EDTA pH 7.0 containing 1% "Triton X-100". The following procedures were then performed as described by Maniatis et al., [Molecular Cloning, A Laboratory Mannual, Cold Spring Harbor, 1982, N.Y.]. The pollen was phenol extracted twice, then ethanol precipitated. The DNA was collected by centrifugation, and the dried pellet was suspended in 10 mM Tris, 1 mM EDTA pH 7.5.

Gel Electrophoresis. To determine if the pBI221 plasmid DNA remained intact 1 hr and 24 hrs after electroporation into the pollen, the DNA extracts were subjected to electrophoresis on 1% agarose gels submerged in TBE (89 mM Tris borate, 50 mM EDTA pH 8.0). The gels were stained with ethidium bromide and photographed. The gels of the DNA from electroporated and control pollen (Lane 0) as shown in FIG. 1 were compared. A band of DNA of the same size as pBI221 (Lane P) was present in DNA extracted from pollen treated with pBI221 and incubated for 1 hr (Lane 1). Pollen not electroporated with pBI221 contained no DNA homologous to pBI221. The appearance of the plasmid DNA as a distinct DNA in pollen extracts 1 hr after electroporation provides further evidence that pBI221 was incorporated into the pollen.

The disappearance of the distinct plasmid DNA band in pollen incubated for 24 hrs suggested that the plasmid DNA was either incorporated into the pollen genomic DNA or degraded. Data from Southern blots indicate that the plasmid DNA was incorporated. The DNA agarose gel lane containing lambda DNA was used for molecular weight comparisons.

Figure 2:
FIG. 2 is an autoradiograph of a Southern blot of the gel from FIG. 1 hybridized with $^{32}$P-labeled GUS DNA.

Southern Blot. The extracted DNA described above was transferred to Biotrans nylon membranes and hybridized with $^{32}$P-labeled pBI221. The autoradiograph shown in FIG. 2 indicates that pollen electroporated in the absence of pBI221 (untreated control) contained no DNA homologous to pBI221 (lane 0). In contrast, pollen subjected to electroporation in the presence of pBI221 (DNA treated) then incubated an additional hour, contained significant amounts of intact pBI221 (lane 1). Furthermore, when the electroporated pollen are incubated for 24 hrs in germination medium, pBI221 appears to be integrated into the pollen genome as evidenced by the presence of high molecular weight pBI221 sequences present on the Southern blot (lane 24). Lane P represents the naked plasmid.

EXAMPLE 2

Preliminary experiments using corn have demonstrated that the gene transfer technique of pollen transformation using electroporation is also effective in monocots which are currently recalcitrant to other gene transfer procedures. Sweet corn pollen was electroporated in the presence of cloned DNA containing the kanimycin biochemical marker gene by subjecting it to a single exponential pulse of 100 μF at either 1.25 Kv or 1.88 Kv supplied by a BTX Model 300 pulse generator substantially by the procedure described in Example 1. The germinating pollen was resuspended in medium containing 2 μg of kanimycin DNA cloned in E. coli. The results of seed production are shown in Table II, below.

TABLE II

Production of seed in corn by pollinating receptive flowers using germinating pollen subjected to an electroporation pulse capable of incorporating specific DNA present in the culture media.

| Treatment | DNA | Seed Production |
|---|---|---|
| Dry pollen | 0 | 74 |
| Pollen in media | 0 | 159 |
| 1.25 Kv pulsed pollen | 2 μg | 72 |
| 1.88 Kv pulsed pollen | 2 μg | 13 |

EXAMPLE 3

Pollen Treatment

Pollen was collected from tobacco Nicotiana gossie L. Domin and germinated for 1 hr substantially as described in Example 1. A sterile cuvette containing 4 mg of the germinated pollen in a final volume of 300 μl of germination medium was electroporated in the presence of 10 μg of the linearized plasmid of pBI221 containing the gene encoding GUS by the procedure of Example 1.

Pollination and Plant Generation

The electroporated pollen was used to pollinate tobacco plants by pipetting about 20 μl of the pollen-containing medium onto the stigma of emasculated flowers. Seeds developed from fertilized ova were collected and planted in individual pots. Mature plants developed in 3–4 mo.

E-Scan Assay

Figure 3:
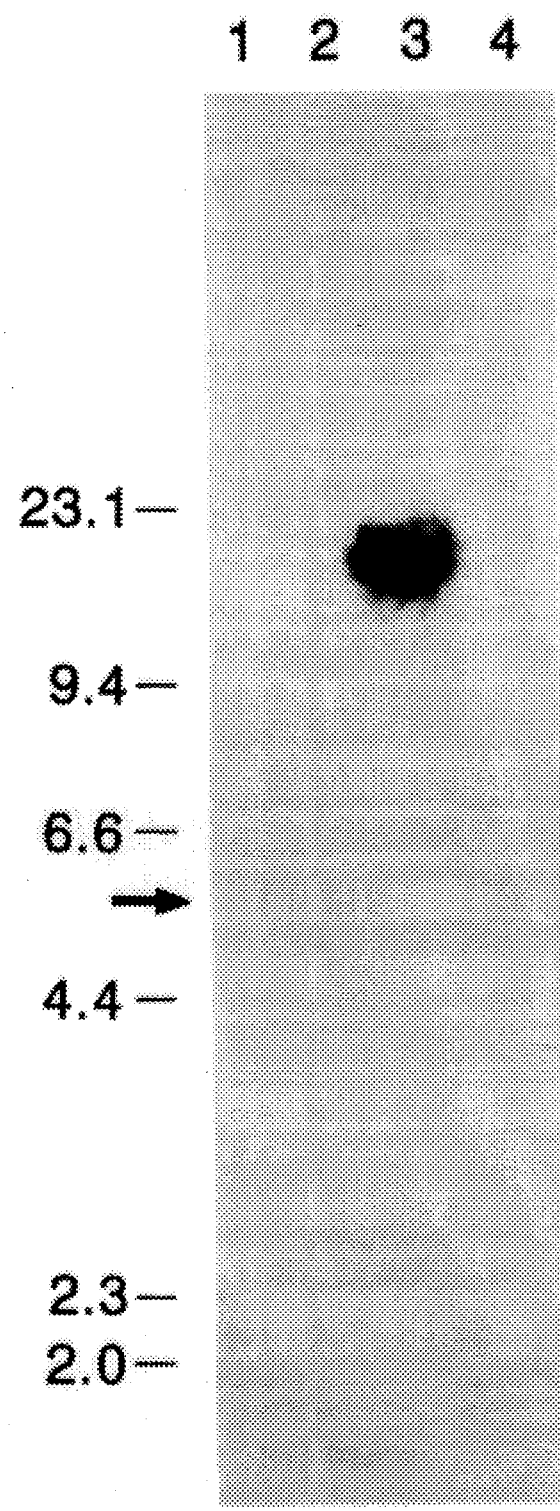
FIG. 3 is a beta-scan of an agarose gel comparing DNA extracts from transformed and untransformed tobacco plant leaf tissue.

Leaves were harvested from the test plants and ~1-g samples were prepared for extraction by grinding the leaf tissue in 100 mM Tris-HCl, containing 100 mM EDTA, 3% SDS, and 1% β-mercaptoethanol at pH 8.0. The leaf suspension was extracted immediately with an equal volume of phenol saturated with 10 mM Tris-HCl (pH 7.5). The aqueous phase was heated at 55° C. for 15 min and extracted with an equal volume of chloroform:isoamyl alcohol (20:1). The DNA was precipitated by the addition of ½ volume of 7.5M ammonium acetate and 1 volume of isopropanol at −70° C. and was collected by centrifugation for 10 min at 10,000× g. The ethanol was decanted and the dried pellet was suspended in 10 mM Tris-HCl, containing 1 mM EDTA pH 8.0. The DNA extracts were digested with EcoRI and subjected to electrophoresis at 70 V for 1 hr on 0.8% agarose gels in 40 mM Tris-acetate buffer, containing 10 mM EDTA pH 8.0. DNA was visualized on the gels by staining with 0.5 μg/ml ethidium bromide and backlighting the gel with UV light. The DNA was blotted onto Biotrans nylon membranes and hybridized with $^{32}$P-labelled DNA encoding GUS. $^{32}$P-labelled probe was made using 1798 bp of the UidA gene contained between bp 20 and bp 1818. After hybridization, the membrane was washed at 55° C. in 2×SSC with 1% SDS (three changes) over 2 hrs. Bound $^{32}$P-label was detected and imaged (FIG. 3) using a computerized "Betascope 603" blot analyzer (Betagen Corp.). DNA segment size markers (kb) were provided by digesting lambda DNA with HindIII (lane 1). Location of the transforming plasmid digested with EcoRI (5.7 kb) is indicated by the arrow. Hybridization of the $^{32}$P-labelled probe to DNA extracts from transformed plants (lane 3) vs nonhybridization in untransformed plants (lanes 2 and 4) is apparent from FIG. 3.

EXAMPLE 4

Figure 4:
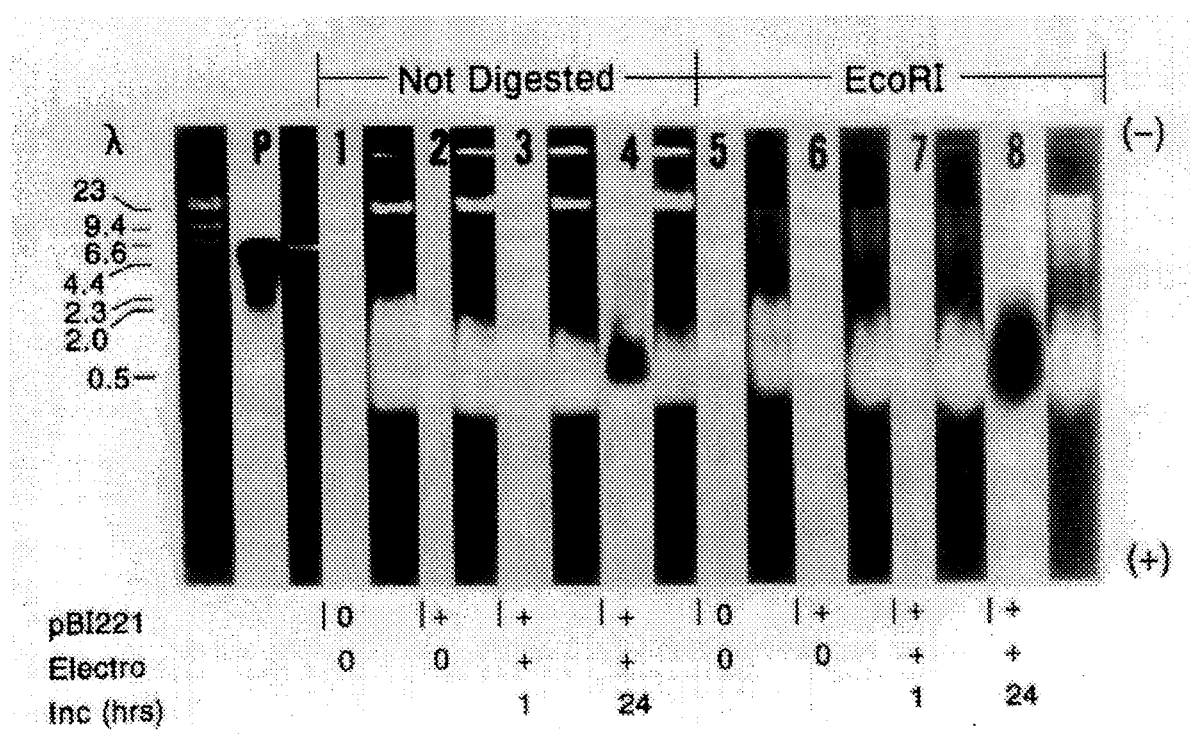
FIG. 4 is an autoradiogram and agarose gel plate of variously treated tobacco pollen.

In Example 1, the possibility existed that active nucleases present on the cell wall of the pollen could be responsible for degradation of the plasmid DNA during uptake. To evaluate this possibility, a series of pollen treatments was conducted. The procedure of Example 1 was repeated using either undigested pBI221 DNA or pBI221 DNA which was linearized by digestion with EcoRI. The DNA was added to the electroporation medium at a concentration of 25–50 µg/ml. After electroporation the pollen were treated with DNase, washed thoroughly, and the pollen DNA was extracted and analyzed by gel electrophoresis and by blotting and hybridization techniques. FIG. 4 is an autoradiogram (white background) of a blot containing DNA and RNA and its corresponding agarose gel (dark background) stained with ethidium bromide and backlighted with UV light. DNA was extracted from pollen which was (+) or was not (0) treated with pBI221 and electroporated. The blot was hybridized against $^{32}$P-labelled DNA probe representing a 1798 bp segment of the UidA gene encoding GUS. DNA extracts shown in lanes 1–4 are not digested with EcoRI; 5–8 are digested with EcoRI. Lanes (1, 5) no pBI221, no electroporation; lanes 2, 6 pBI221 added, no electroporation; lanes 3, 7 pBI221 added, electroporated, incubated 1 hr; lanes 4, 8 pBI221 added, electroporated, incubated 24 hr. The positions of lambda molecular weight markers are indicated and pBI221 plasmid (P) digested with EcoRI is present as a location marker.

The Southern blot containing the pollen DNA 24 hr after electroporation with pBI221 showed that high molecular weight DNA (lane 4) hybridized with the probe. This indicated that some of the pBI221 may have been integrated into the pollen DNA. Pollen DNA digested with EcoRI on the same blot hybridized to the GUS-specific DNA probe as lower molecular weight DNA of different sizes (lane 8), again supporting the hypothesis that some of the pBI221 DNA had integrated into the pollen DNA as expected. The probe did not hybridize to the DNA from the control pollen (lanes 1, 2, 5, and 6). This demonstrated that DNA at least the size of the GUS plasmid (5.7 kb) could be incorporated directly into the germinating pollen. The same gel also contained RNA. Pollen electroporated with pBI221 (lanes 3, 4, 7, and 8) contained RNA which hybridized with the DNA probe encoding GUS 1 hr and 24 hr after electroporation. This indicates, at a minimum, transient transcription of the inserted gene. The levels of RNA specific to the probe increased significantly between 1 and 24 hr after electroporation.

EXAMPLE 5

To determine the transformation efficiency of the pollen electroporation process, samples of leaf tissue collected from the plants grown in Example 3 were assayed for expression of GUS. Approximately 0.5 g of leaf tissue was suspended in 2.5 ml of GUS extraction buffer containing 50 mM NaPO$_4$, pH 7.0, 10 mM EDTA, 0.1% (v/v) "Triton X-100", and 10 mM β-mercaptoethanol, thoroughly ground in a chilled mortar and centrifuged at 2500×g for 10 min. Both the supernatant fraction and the resuspended pellet were assayed for GUS activity in GUS extraction buffer at 37° C. The reaction mixture consisted of 500 µl of 1 mM 4-methyl umbelliferyl β-D-glucuronide in lysis buffer and 200 µl of the pollen extract. The reaction was stopped by the addition of 0.2M Na$_2$CO$_3$ to bring the final volume to 2.0 ml. The activity was measured fluorometrically using wavelengths of 365 and 455 nm for excitation and emission, respectively. Quantitating of activity was established from a standard curve using umbelliferone as a standard. The results of four replicate analyses (two samples, two assays each) are reported in Table III below. Of 245 plants surveyed, 108 (44.1%) demonstrated GUS activity more than twice the level found in control plants which were electroporated in the absence of DNA.

TABLE III

| Gus Activity in Pollen Transformed Tobacco Plants | | |
| --- | --- | --- |
| Fraction | pm/GFW/hr[a] | nm/mg Pro/hr[b] |
| supernatant | 32.6 (74.7)[c] | 0.6 (3.6) |
| pellet | 76.8 (94.7) | 1.7 (7.1) |

[a]Picomoles of umbelliferone per gram fresh weight leaf tissue per hr.
[b]Nanomoles of umbelliferone per mg protein per hr.
[c]Numbers in parentheses represent standard deviation of all samples assayed after twice the control activity was subtracted from the treatment sample. The comparatively large standard deviations illustrate that many of the samples demonstrated GUS activity substantially in excess of twice the activity of the controls.

It is understood that the foregoing detailed description is given merely by way of illustration and that modification and variations may be made therein without departing from the spirit and scope of the invention.

We claim:

1. A method for transforming a plant with a foreign DNA comprising:
   a. introducing said foreign DNA into pre-germinated pollen by electroporation, wherein said foreign DNA is in an expression vector and is capable of participating in a recombination event with the native DNA in said pollen and wherein said pollen is capable of fertilizing ova of the plant;
   b. fertilizing ova of the plant; and
   c. selecting for germplasm which is transformed with said foreign DNA.

2. A method as described in claim 1 wherein said pollen and said ova are from the same plant line.

3. A method as described in claim 1 and further comprising collecting seed resulting from step (b), propagating said seed into plants, and using said plants for the selecting in step (c).

4. The method as described in claim 1, wherein said plant is selected from the group consisting of field crops, horticultural crops and orchard crops.

5. The method of claim 1, wherein said plant is tobacco.

6. The method of claim 5, wherein said foreign DNA is the gene encoding GUS.

7. A method for introducing foreign DNA into a plant comprising:
   a. introducing said foreign DNA into pre-germinated pollen by electroporation, wherein said pollen is capable of fertilizing ova of the plant;
   b. fertilizing ova of the plant; and
   c. selecting for expression of said foreign DNA.

8. The method of claim 7, wherein said pollen and said ova are from the same plant line.

9. The method of claim 7, wherein said plant is selected from the group consisting of field crops, horticultural crops and orchard crops.

10. The method of claim 7, wherein said plant is tobacco.

11. The method of claim 7, wherein said plant is corn.

12. The method of claim 1, wherein said plant is corn.

* * * * *